United States Statutory Invention Registration [19]

[11] Reg. Number: H618

Merkel

[43] Published: Apr. 4, 1989

[54] INTERPUPILLARY DISTANCE MEASURING DEVICE

[75] Inventor: Harold S. Merkel, Beavercreek, Ohio

[73] Assignee: The United States of America as represented by the Secretary of the Air Force, Washington, D.C.

[21] Appl. No.: 119,877

[22] Filed: Nov. 5, 1987

[51] Int. Cl.[4] ..... A61B 3/10

[52] U.S. Cl. ..... 351/204; 33/200

[58] Field of Search ..... 351/204; 33/200

[56] References Cited

U.S. PATENT DOCUMENTS

| | | | |
|---|---|---|---|
| 1,327,163 | 1/1920 | Mathewson et al. . | |
| 2,361,534 | 10/1944 | Eppenstein . | |
| 2,380,263 | 7/1945 | Rees | 351/204 |
| 4,212,538 | 7/1980 | Esmond . | |
| 4,244,639 | 1/1981 | Kanda . | |
| 4,364,645 | 12/1982 | Feinbloom . | |
| 4,626,088 | 12/1986 | Joncour et al. . | |

FOREIGN PATENT DOCUMENTS

| | | | |
|---|---|---|---|
| 957854 | 9/1982 | U.S.S.R. | 351/204 |

*Primary Examiner*—Stephen C. Buczinski
*Assistant Examiner*—Linda J. Wallace
*Attorney, Agent, or Firm*—Bobby D. Scearce; Donald J. Singer

[57] ABSTRACT

An instrument for measuring the interpupillary distance of a subject is described which comprises two parallel sighting tubes disposed in adjustable spaced relationship along parallel optical axes and interconnected for measuring the spacing between the axes, two eyepiece lenses of preselected equal focal length disposed at corresponding first ends of the sighting tubes, first and second translucent targets bearing recognizable indicia disposed along respective sighting tubes a distance from the lenses equal to the focal length, and an aperture near each lens for limiting the size of the field of view along each optical axis.

3 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INTERPUPILLARY DISTANCE MEASURING DEVICE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to clinical instruments for the examination of eyes, and more particularly to a portable instrument for measurement of the interpupillary distance.

Interpupillary distance measurements are made by opticians, optometrists and ophthalmologists for clinical purposes, prescriptions for eyeglasses, and similar and related purposes. Previously available devices for measurement of interpupillary distances may be exemplified by those described by or referenced in U.S. Pat. Nos. 2,361,534 and 4,244,639. Existing devices normally require a separate operator to focus and/or align the optics thereof, to make measurements and to interpret results.

The invention provides a simple, cost effective, accurate and reliable subject operated instrument for measurement of the interpupillary distance. The invention presents recognizable optical images to respective eyes of a subject sighting along the optical axes of a pair of parallel sighting tubes. The tubes are movable with respect to each other and are interconnected by a scale for displaying the spacing between the optical axes. The subject adjusts the separation of the tubes until the images appear superimposed and reads the interpupillary distance from the scale.

It is, therefore, a principal object of the invention to provide an improved eye examinaton instrument.

It is another object of the invention to provide a subject operated instrument for measurement of the interpupillary distance.

These and other objects of the invention will become apparent as the detailed description of representative embodiments proceeds.

SUMMARY OF THE INVENTION

In accordance with the foregoing principles and objects of the invention, an instrument for measuring the interpupillary distance of a subject is described which comprises two parallel sighting tubes disposed in adjustable spaced relationship along parallel optical axes and interconnected for measuring the spacing between the axes, two eyepiece lenses of preselected equal focal length disposed at corresponding first ends of the sighting tubes, first and second translucent targets bearing recognizable indicia disposed along respective sighting tubes a distance from the lenses equal to the focal length, and an aperture near each lens for limiting the size of the field of view along each optical axis.

DESCRIPTION OF THE DRAWINGS

The invention will be clearly understood from the following detailed description of representative embodiments thereof read in conjunction with the accompanying drawings wherein.

DETAILED DESCRIPTION

Figure 1:
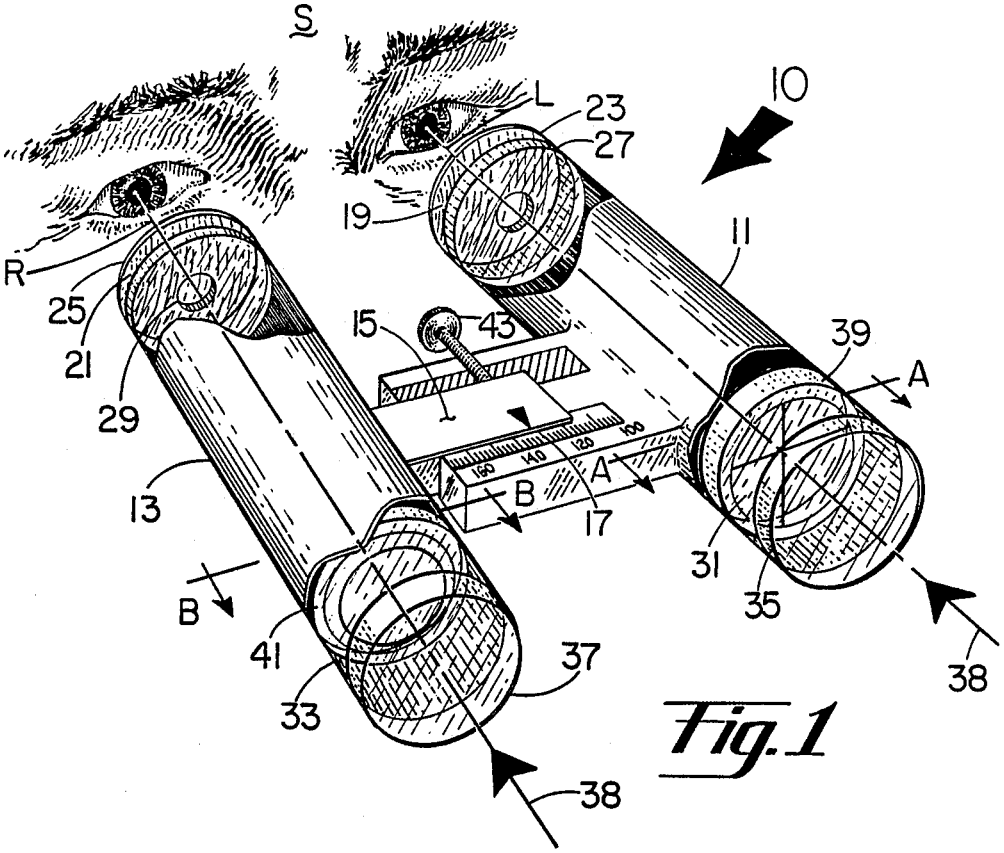
FIG. 1 is a schematic in partial cutaway of a binocular interpupillary distance measuring instrument of the invention.

Referring now to the drawings, shown in FIG. 1 is a schematic in partial cutaway of binocular interpupillary distance measuring instrument 10 of the invention. Instrument 10 comprises two sighting tubes 11,13 disposed along parallel optical axes L,R for viewing by respective left and right eyes of subject S. Tubes 11,13 are connected to corresponding elements of a movable indicator 15 and scale 17 which hold tubes 11,13 in adjustable parallel spaced relationship. Scale 17 is calibrated to provide a direct reading of the spacing between axes L,R (interpupillary distance). At respective first ends 19,21 of tubes 11,13 are mounted eyepiece lenses 23,25 having equal preselected focal length f. Apertures 27,29 disposed near respective lenses 23,25 limit to preselected size the available solid viewing angle along axes L,R. Second ends 31,33 of tubes 11,13 include translucent light diffusing disks 35,37 for diffusing ambient light 38 admitted into tubes 11,13 along axes L,R. Targets 39,41 are disposed along tubes 11,13 a distance equal to focal length f from lenses 23,25 for simultaneous viewing by respective left and right eyes of subjects. Targets 39,41 each comprise a recognizable indicia on a translucent disk.

Figure 1A:
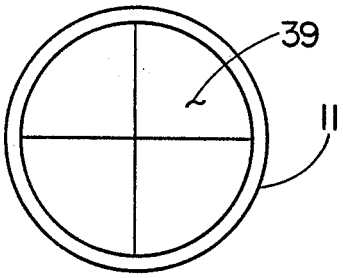
FIG 1*a* is a view of the instrument of FIG. 1 along line A—A.
Figure 1B:
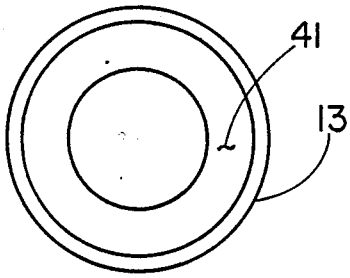
FIG 1*b* is a view of the instrument of FIG. 1 along line B—B.

FIGS. 1*a*,1*b* are views of instrument 10 along lines A—A and B—B showing representative configurations for respective targets 39,41. Target 39 may comprise a circle and cross. while target 41 may comprise two concentric circles. Other combinations of targets may be used as would occur to one with skill in the field of the invention, so long as the superposition (binocular fusion) of the images as viewed by subject S along axes L,R is easily identified. Targets 39,41 must be different to ensure that subject S does not mistake suppression of one eye for fusion of the targets.

Figure 2:
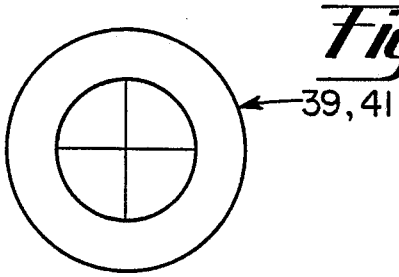
FIG. 2 is a superposition of images as viewed by a subject in the use of the instrument of FIG. 1.

In the use of instrument 10 for measuring the interpupillary distance, subject S views targets 39,41 along respective axes L,R and adjusts the spacing of tubes 11,13 using adjusting screw 43 until targets 39,41 appear superimposed as suggested in FIG. 2. The interpupillary distance is read directly from calibrated scale 17.

The invention therefore provides a novel subject operated instrument for measurement of the interpupillary distance. It is understood that modifications to the invention as described may be made as would occur to one with skill in the field of the invention within the scope of the appended claims. All embodiments contemplated hereunder which accomplish the objects of the invention have therefore not been shown in complete detail. Other embodiments may be developed without departing from the spirit of the invention or from the scope of the claims.

I claim:

1. An instrument for measuring the interpupillary distance of a subject, comprising:

(a) a first sighting tube and a second sighting tube disposed in adjustable parallel spaced relationship along respective parallel first and second optical axes;

(b) means interconnecting said first tube and said second tube for selectively adjusting said first tube in said adjustable parallel spaced relationship relative to said second tube and for gauging the spacing between said first and second optical axes;

(c) a first eyepiece lens and a second eyepiece lens, having equal preselected focal lengths, disposed along respective said first and second optical axes at corresponding first ends of said first sighting tube and said second sighting tube; and (d) a single first translucent target bearing a first recognizable indicia disposed within said first tube along said first optical axis a distance equal to said preselected focal length from said first lens, and a single second translucent target bearing a second recognizable indicia different from said first recognizable indicia disposed within said second tube along said second optical axis a distance equal to said preselected focal length from said second lens, said first recognizable indicia and said second recognizable indicia being optically fusible by said subject sighting along respective said first and said second optical axes by spacing said first sighting tube and said second sighting tube a distance corresponding to the interpupillary distance of said subject.

2. The instrument of claim 1 further comprising first and second apertures of equal preselected size disposed adjacent respective said first lens and said second lens for limiting the angular field of view along each of said first and second optical axes to preselected size.

3. The instrument of claim 1 further comprising means disposed at corresponding second ends of said first tube and said second tube for admitting diffuse light into said first tube and said second tube along respective said first and second optical axes for diffusely illuminating said first target and said second target.

* * * * *